(12) United States Patent
Korotko et al.

(10) Patent No.: US 6,647,986 B1
(45) Date of Patent: Nov. 18, 2003

(54) WRIST SPLINT AND HEMOSTASIS DEVICE

(75) Inventors: Joseph R. Korotko, Troy, MI (US); William W. O'Neill, Grosse Point Farms, MI (US); Steve L. Almany, West Bloomfield, MI (US)

(73) Assignee: Accumed Systems, Inc., Ann Arbor, MI (US)

( * ) Notice: Subject to any disclaimer, the term of this patent is extended or adjusted under 35 U.S.C. 154(b) by 0 days.

(21) Appl. No.: 09/786,893

(22) PCT Filed: Sep. 9, 1999

(86) PCT No.: PCT/US99/20754
§ 371 (c)(1),
(2), (4) Date: May 14, 2001

(87) PCT Pub. No.: WO00/15160
PCT Pub. Date: Mar. 23, 2000

Related U.S. Application Data
(60) Provisional application No. 60/099,956, filed on Sep. 11, 1998.

(51) Int. Cl.$^7$ .................................................. A61F 5/37
(52) U.S. Cl. ........................... 128/877; 28/878; 28/879; 602/23
(58) Field of Search ...................... 602/20, 21; 128/869, 128/876, 877–879; 604/174

(56) References Cited

U.S. PATENT DOCUMENTS

| | | | |
|---|---|---|---|
| 4,425,913 A | 1/1984 | Lewis | 128/133 |
| 4,677,971 A | 7/1987 | Lindemann | 128/87 |
| 4,760,846 A | 8/1988 | Mers Kelly et al. | 128/327 |
| 4,798,199 A | 1/1989 | Hubbard et al. | 128/87 R |
| 5,025,801 A | 6/1991 | Callaway | 128/877 |
| 5,269,803 A | 12/1993 | Geary et al. | 606/201 |
| 5,413,120 A | 5/1995 | Grant | 128/877 |
| 5,601,597 A | 2/1997 | Arrowood et al. | 606/203 |
| 5,623,951 A | 4/1997 | Kamaya | 128/877 |
| 5,730,152 A | 3/1998 | Esser | 128/845 |

FOREIGN PATENT DOCUMENTS

DE  3117090  * 12/1982

* cited by examiner

Primary Examiner—Michael A. Brown
(74) Attorney, Agent, or Firm—Hayes Soloway P.C.

(57) ABSTRACT

A hand/wrist positioning splint to keep the hand positioned for radial artery access and to permit application of a hemostasis band to apply pressure to the radical artery puncture site to permit closing of said puncture site, is provided. The splint includes a rigid structure (12A) for positioning a patient's hand, and wrist in a fixed hyper-extended state, the structure (12A) having a distal end surface to support a patient's hand, and palm up, the end surface extends downwardly from the wrist position to make a first fixed angle with a horizontal plane. The rigid structure also has a wrist/forearm support surface also extending downwardly from the wrist position to make a second fixed angle with a horizontal plane. Straps (16A) are provided for securing the hand, and the wrist/forearm in fixed position on the rigid structure. An opening (20A) in the wrist/forearm surface of the rigid support below the point of arterial access permits application of a hemostasis band to the arterial puncture site.

17 Claims, 11 Drawing Sheets

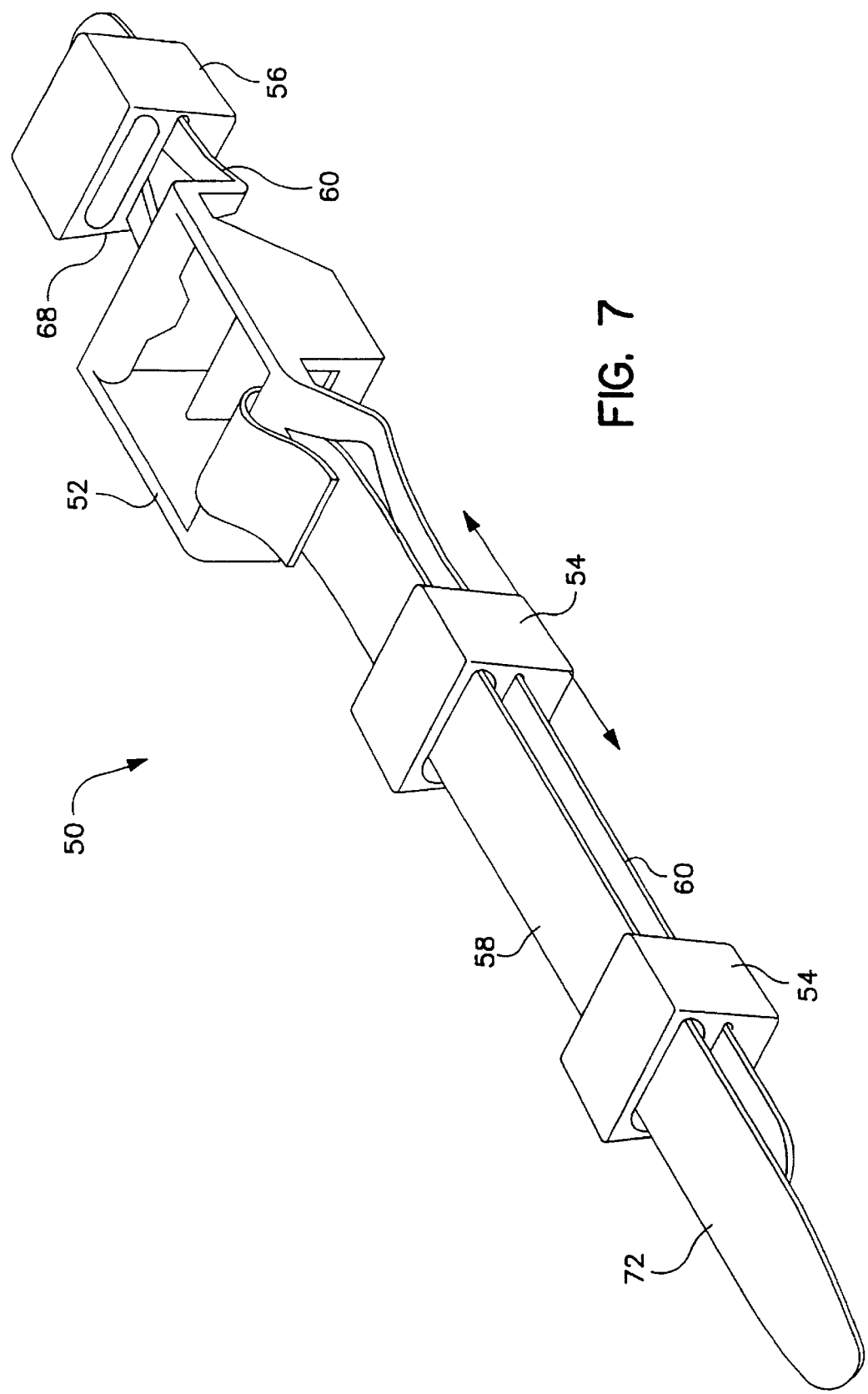

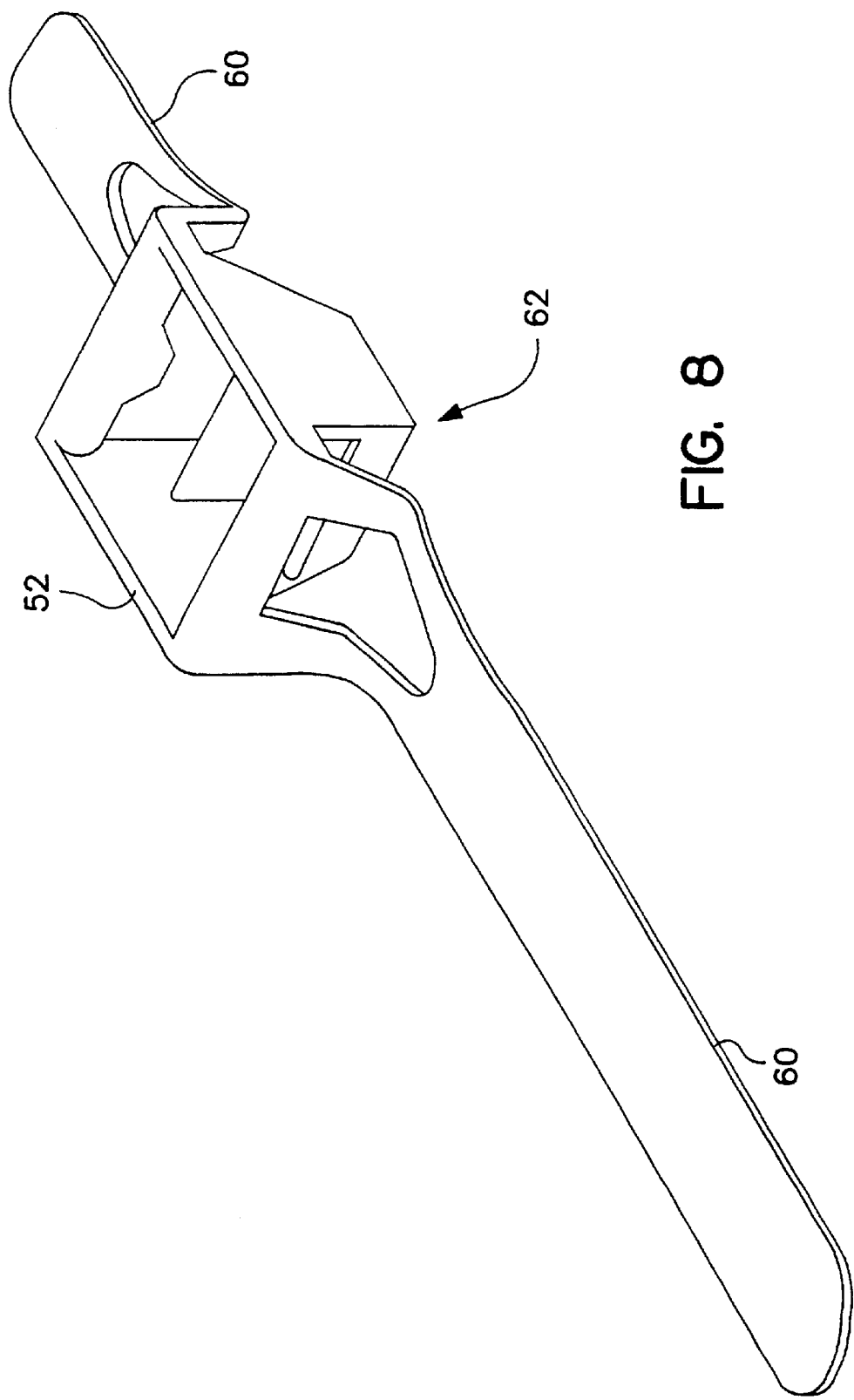

WRIST SPLINT AND HEMOSTASIS DEVICE

This application claims the benefit of provisional application 60/099,956 filed Sep. 11, 1998.

SUMMARY OF THE INVENTION

The present invention relates to devices for use during and after radial artery procedures. More particularly, the present invention is directed to a hand/wrist positioning splint that keeps the hand positioned for radial artery access, and a hemostasis band to apply pressure to the radial artery puncture site to permit closure of the site. Particular utility of the present invention is in radial artery procedures, e.g., intervention cardiology, diagnostic cardiology, radiology, etc., and other coronary/cardiac procedures; although other utilities are contemplated herein In one aspect, the present invention provides a hand/wrist positioning splint that is shaped to position the hand and wrist in a hyperextended state during radial procedures and to keep the hand and wrist immobilized during the procedure. Advantageously, the splint of the present invention positions the hand and wrist in such a manner so as to extend the radial artery for simple, safe ingress during radial artery procedures. In the preferred embodiment, Velcro straps or suction cups are provided to ensure the immobility of the hand/wrist and to ensure the wrist splint does not move during the procedure. Also preferably, the splint is formed of biocompatible material that is presterilized.

In another aspect, the present invention provides a hemostasis band which is advantageously designed to apply pressure directly to the puncture wound site of the radial artery to prevent bleeding and permit closure of the wound. Also advantageously, the hemostasis band has features that permit sufficient pressure to be applied to the radial artery (so that the wound can close) while maintaining blood flow through the radial artery (or, for that matter, through the ulnar artery or venous system). Preferably, the hemostasis band is formed of biocompatible material that is presterilized and disposable for single-use applications. In yet another aspect of the present invention, the wrist splint and hemostasis band are provided in one integrally formed device.

It will be appreciated by those skilled in the art that although the following Detailed Description will proceed with reference being made to preferred embodiments, the present invention is not intended to be limited to these preferred embodiments. Other features and advantages of the present invention will become apparent as the following Detailed Description proceeds, and upon reference to the Drawings, wherein like numerals depict like parts, and wherein:

BRIEF DESCRIPTION OF THE DRAWINGS

FIG. 7 is an elevational view of the hemostasis band of the present invention;

FIG. 8 is an elevational view of one preferred embodiment of the buckle of the hemostsis band of the present invention;

DETAILED DESCRIPTION OF THE INVENTION

Figure 1:
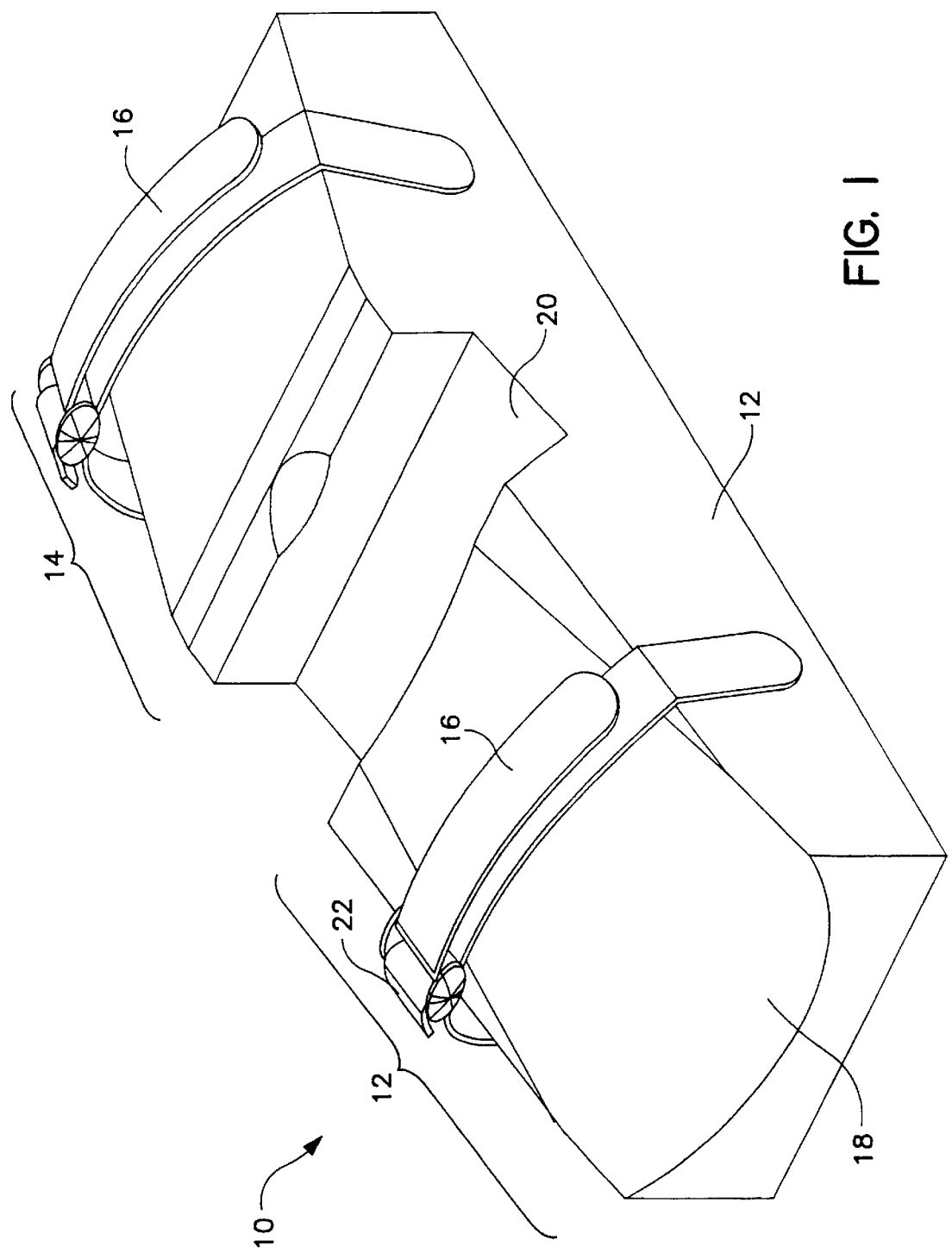
FIG. 1 is an elevational view of one preferred embodiment of the splint of the present invention.

FIGS. 1–3A depict various views of the wrist splint 10 of the present invention. Essentially, splint 10 comprises an elongated member 12, having a proximal end 12 and a distal end 14. Two or more straps 16 are provided, positioned on the distal 14 and proximal 12 ends to secure a patient's hand and wrist/forearm, respectively, to the splint 10. In this embodiment, the splint is a solid, form-fitted, integrally molded piece. An indent 18 is formed on the proximal end to mate with the shape of a patient's wrist/forearm, as shown in FIG. 2A. Preferably, member 12 is a one piece member integrally formed of foam rubber or other similar soft, pliable material. Although not shown in the drawings, a non-bending member of appropriate stiffness can be removably affixed to the bottom of member 12 to prevent any bending of member 12 during use. Of course, member 12 can be permanently affixed (to prevent bending) to an operating table, etc. without departing from the present invention. A cavity 20 is provided between the distal and proximal ends to facilitate attachment of a hemostasis band about the wrist (discussed more fully below) or other device used during a radial artery procedure.

Straps 16 can be any fixable member known in the art, or, as shown in FIG. 1, each strap 16 has a locking clasp 22 to vary the length of the strap 16 to fit the particular patient. It will be understood by those skilled in the art that the strap 16 shown in FIG. 1 is just one of a myriad of equivalent strap structures, for example, Velcro straps, elastic straps, etc., and all such equivalents are deemed within the scope of the present invention. Straps 16 are securely fastened (using epoxy, etc.) to member 12 for repeated use and strength. Alternatively, straps 16 are integrally molded with member 12 (not shown).

Figure 3:
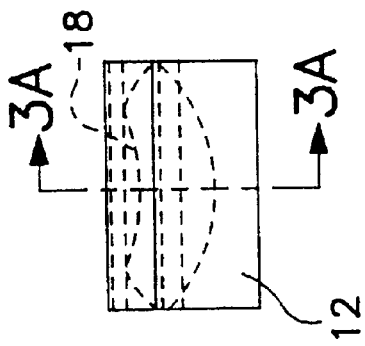
FIG. 3 is a detailed end view of the splint of FIG. 1.
Figure 3A:
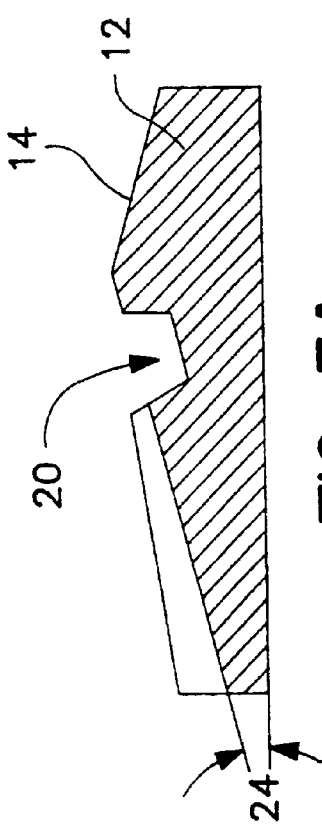
FIG. 3A is an end-on cross sectional view of the splint taken along the lines 3—3 of FIG. 3.
Figure 2:
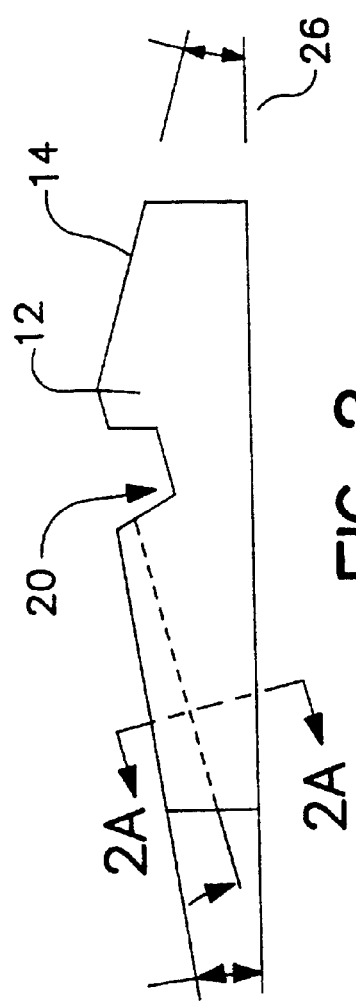
FIG. 2 is a side view of the splint of FIG. 1.
Figure 2A:
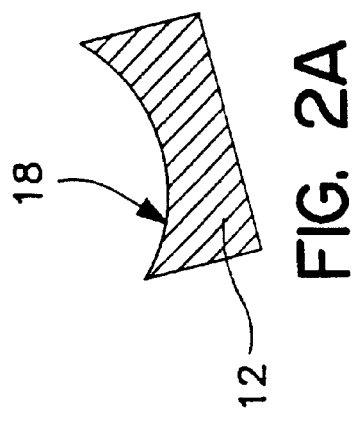
FIG. 2A is a cross-sectional view of the splint view taken along the lines 2—2 of FIG. 2.

As shown in FIG. 2, member 10 is preferably formed with two distinct angles FIG. 3A and 26, formed about the wrist/hand joint location (i.e., formed about cavity 20). It is one object of the present invention to position a patient's hand and wrist in a hyperextended state, thereby increasing the ease for radial artery access and procedures. To that end, angles 24 and 26 permit the hand to be hyperextended to ensure proper exposure of the radial artery. In use, a patients hand, palm up, is placed on the distal end 14 of member 10 and strapped to the member 10 using strap 16. Likewise, the wrist/forearm area is placed into indent 18 of member 10 and strapped in place. Angle 24 and 26 permit the radial artery to be at, or near, a greatest height above the hand and wrist (i.e., fully exposed). In the embodiment of FIGS. 1–3A, angles 24 and 26 are approximately 12 degrees and 25 degrees, respectively.

Figure 4:
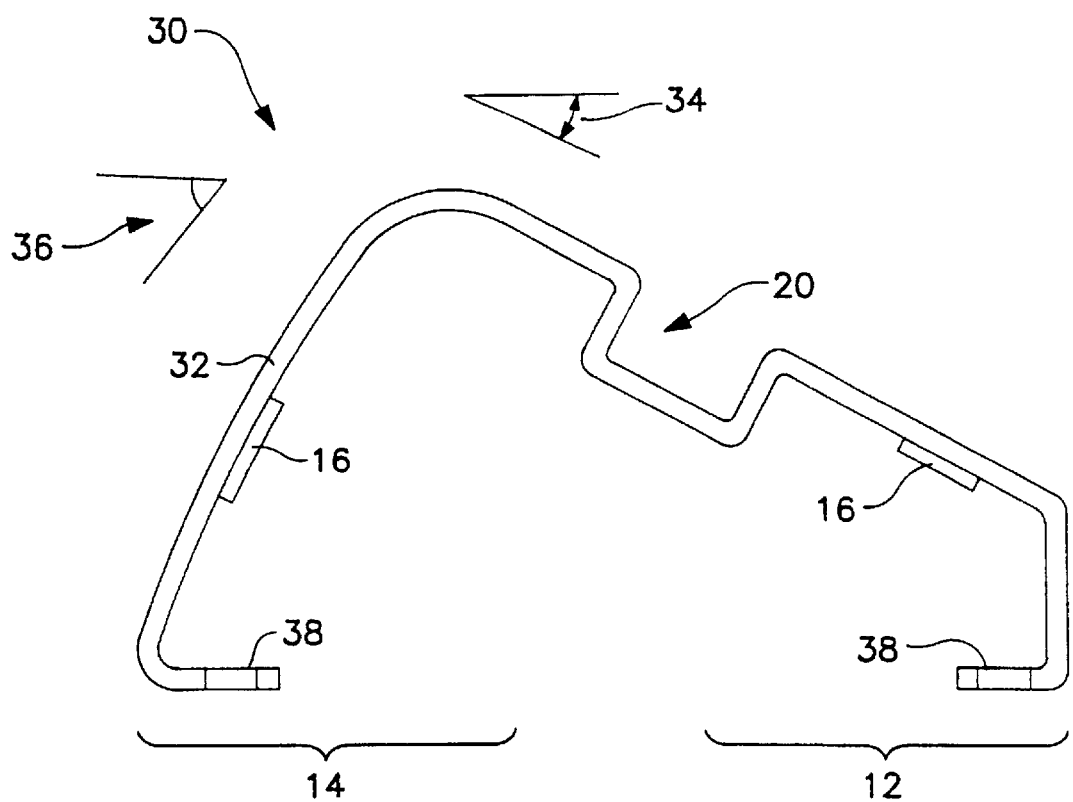
FIG. 4 is a side view of another embodiment of the splint of the present invention.
Figure 6:
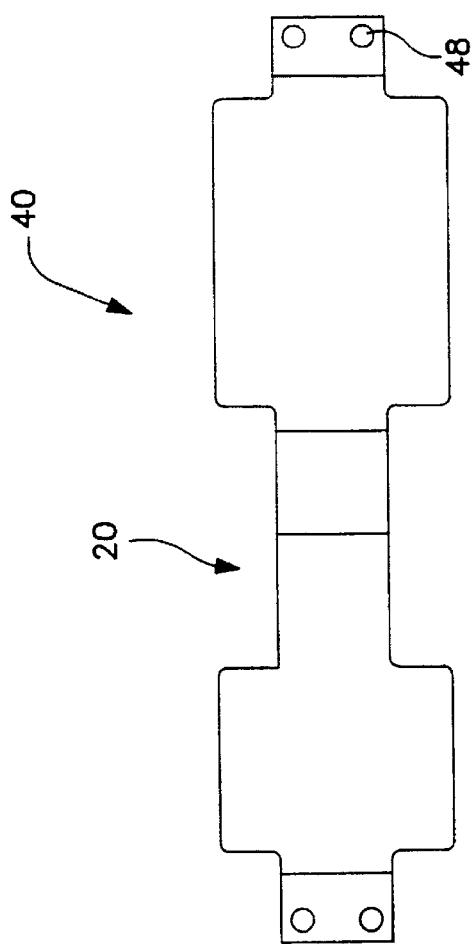
FIG. 6 is top view of the embodiment of FIG. 5.
Figure 5:
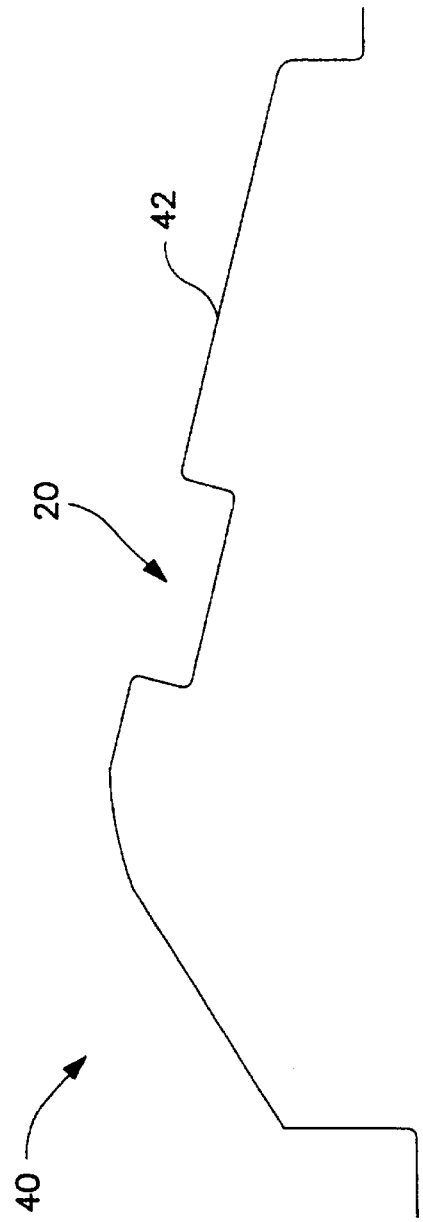
FIG. 5 is a side view of another embodiment of the splint of the present invention.

FIGS. 4 and 5 depict side views of another splint 30 and 40 of the present invention. Splint 30 and 40 are substantially similar to splint 10 (discussed above), except that, in these embodiments, member 32 and 42 are formed of a thin, stiff material (as opposed to the solid body member 12, discussed above). These embodiments also differ in the extension angles for the wrist and hand, for use according to certain needs. Generally, the extension angle disclosed in the above-described embodiments is between 15 and 45 degrees, but can be modified for any angular extension. In other words, angle 34 and 36 are more pronounced than in the previous embodiment, to further hyperextend the hand/wrist. The embodiment of FIG. 5 is likewise modified. FIG. 6 is a top down view of the embodiment of FIG. 5, and is substantially similar to a top down view of FIG. 4, except for the respective angles, as discussed above. It should be noted that the splints of FIGS. 4 and 5 can be affixed to a non-flexing member (not shown), via attachment holes 48, so that the splint 30, 40 does not bend or move. It is intended that the design can be attached to the table, bed or armboard using either a long strap or suction cups or a similar component.

The splint is formed of plastic or other suitable material that is biocompatable and that meets industry standards with regard to tissue and systemic reactivity, toxicity, cytotoxicity and non-pyrogenic. In addition, the splint should be formed of appropriate material that can be sterilized through acceptable means, e.g., ethylene oxide (ETO), gamma, e-beam, etc. Of course, the splint can also be provided in a presterilized state for single-use purposes.

Figure 12:
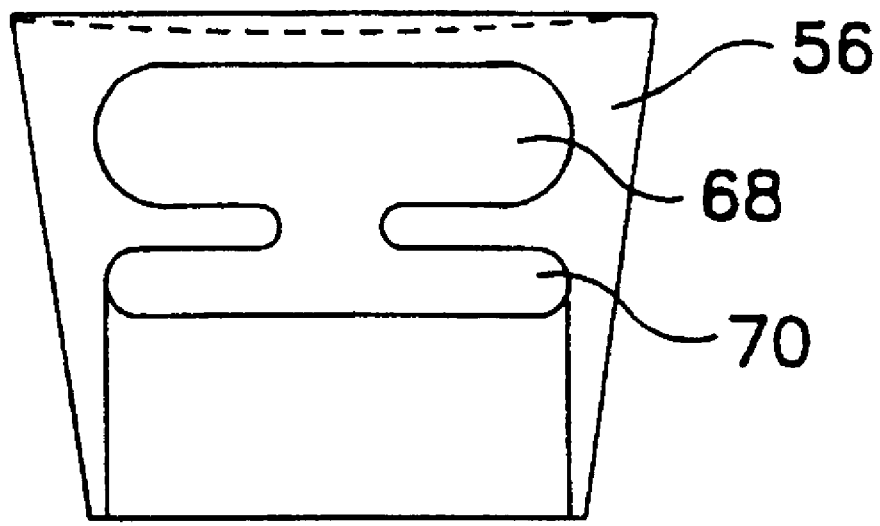
FIG. 12 is a side view of another preferred support pad of the hemostasis band of the present invention.

In another aspect of the present invention, a radial hemostasis band is provided. As shown in FIG. 7, hemostasis band 50 essentially comprises a fixed foam block, a plurality of adjustable foam blocks, a connecting support pad 56, a retaining strap 58, clasp 72 and flexible members 60. Retaining strap 58 is preferably a pliable member that is looped through one or more supporting pads 54, via openings 68 in the support pads (FIG. 12). Also referring to FIG. 12, each support pad 54 and the connecting support pad 56 is slidably affixed to flexible members 60, via slots 70, so that the relative position of the pads can be easily adjusted (as shown by the arrow in FIG. 7). Flexible members 60 are preferably formed to permit bending in the radial direction (i.e., bending about a patient's wrist), but with sufficient mechanical strength to return to a relatively linear position when not in use. As shown in FIG. 8, flexible members 60 are attached to buckle 52, either permanently or removably. Of course, flexible members could also be attached to the buckle 52 by a rotatable boss pin (not shown). The flexible member 60 can be cut shorter if it is too long for patient's with small (skinny) wrists. Cutouts exist in the flexible member 60 to facilitate cutting. To fasten the device about a patient's wrist, a clasp 72 (or other fastening means) is provided on the strap 58 that mates with an opening 68 in the connecting support pad 56 (FIG. 12). Once connected, radial adjustment can be achieved by sliding the connecting support pad 56, thereby tightening the band around the patient's wrist.

Figure 9:
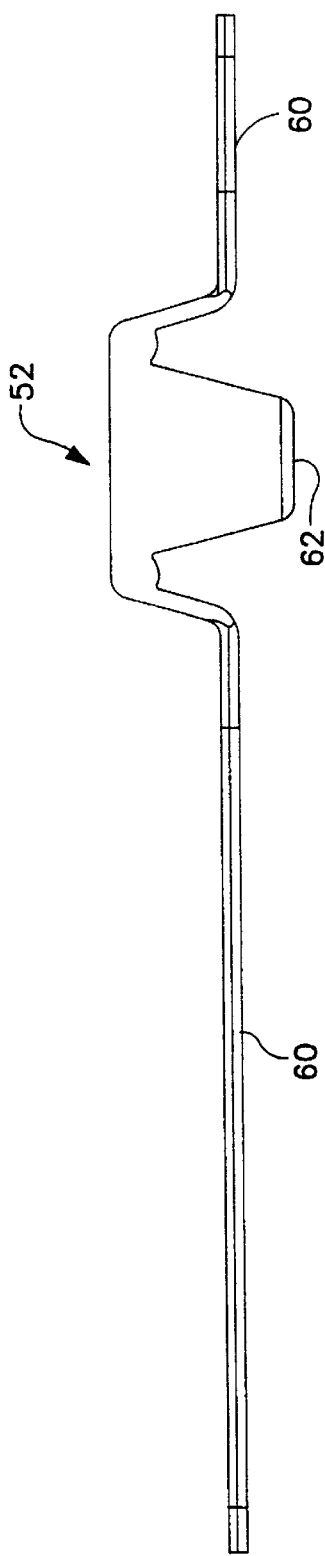
FIG. 9 is a side view of the buckle of FIG. 8.
Figure 10:
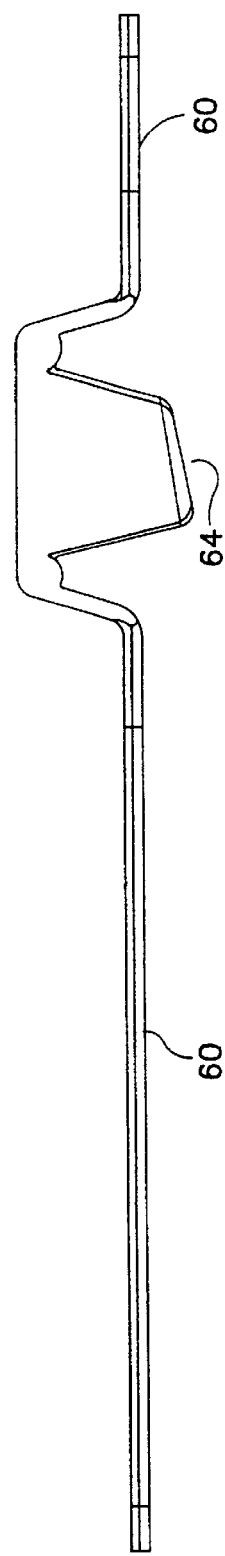
FIG. 10 is a side view of another preferred embodiment of the buckle of the hemostsis band of the present invention.
Figure 11:
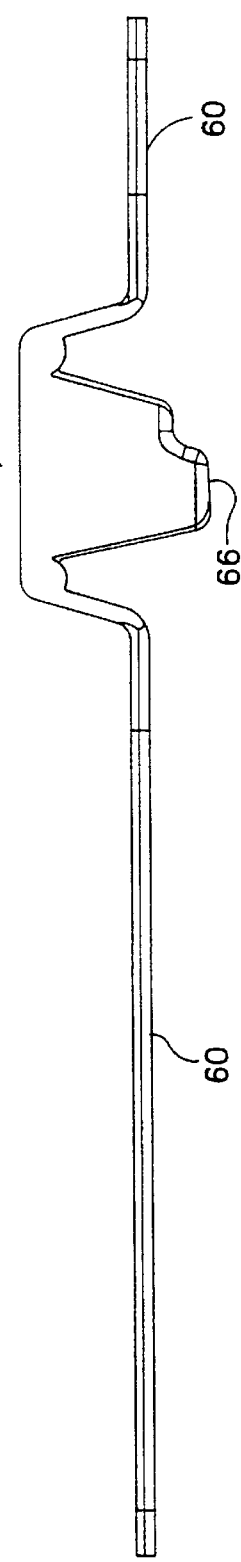
FIG. 11 is a side view of another preferred embodiment of the buckle of the hemostsis band of the present invention.

One object of the hemostasis band 50 is to provide sufficient pressure to close the puncture site of the radial artery after a radial procedure, while maintaining blood flow through the ulnar artery and venous system. To that end, buckle 52 is provided. Side views of various preferred embodiments of the buckle 52 are shown in FIGS. 9–11. Buckle 52 has a generally trapezoidal shape with a bottom end that applies pressure to the radial artery. The bottom end can be flat 62, slanted 64 or partially curved 66, so that, once positioned, pressure is only applied to the radial artery without restricting other local veins and arteries.

As with the splint (discussed above), the hemostasis band is formed of plastic and other suitable material that is biocompatable and that meets industry standards with regard to tissue and systemic reactivity, toxicity, cytotoxicity and non-pyrogenic. In addition, the hemostasis band should be formed of appropriate material that can be sterilized through acceptable means, e.g., ethylene oxide (ETO), gamma, e-beam, etc. Of course, the hemostasis band can also be provided in a presterilized state for single-use purposes.

Figure 13:
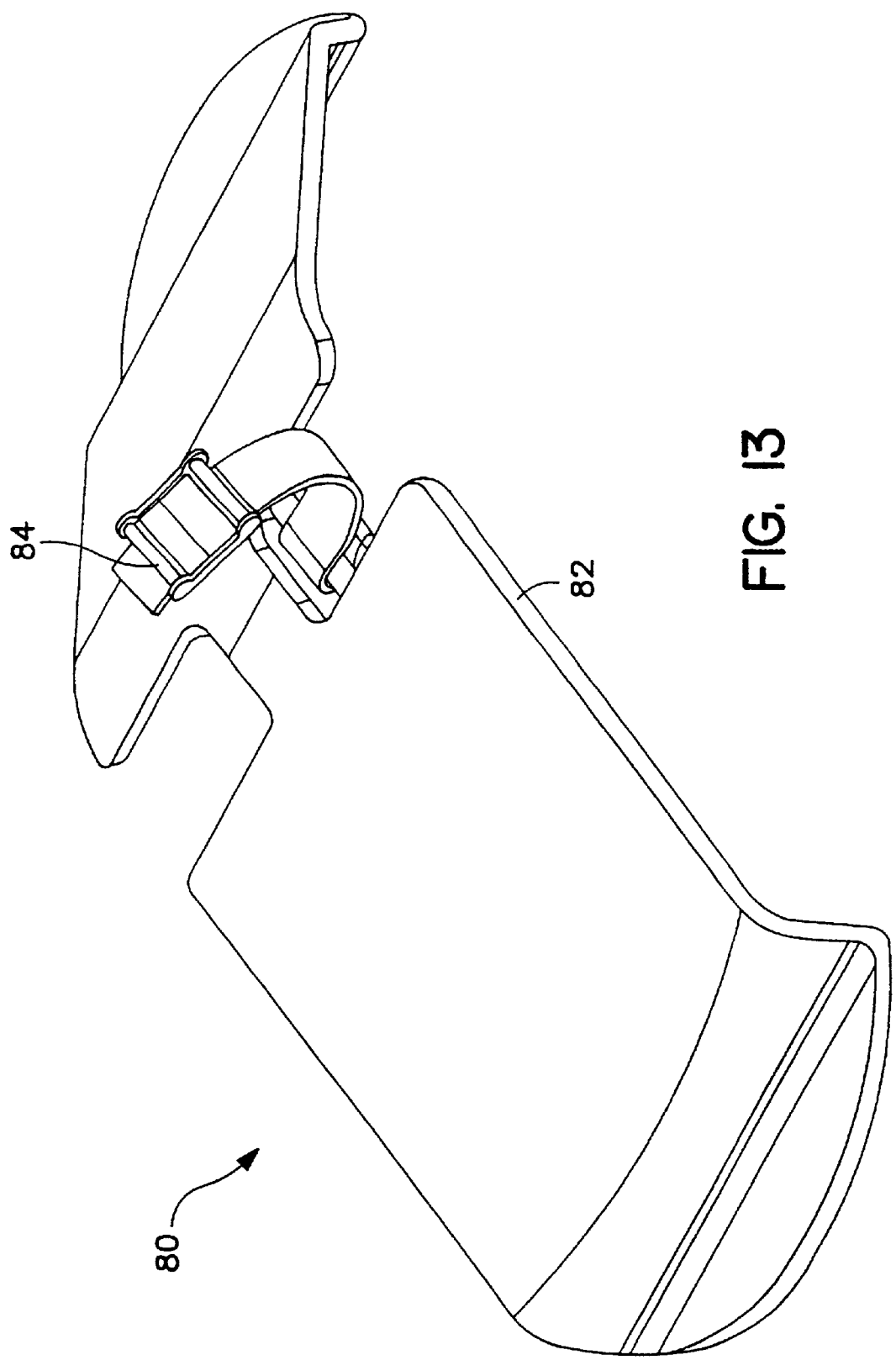
FIG. 13 is an elevational view of another preferred embodiment of the wrist splint in combination with the hemostasis band of the present invention.

Turning now to FIG. 13, another aspect of the present invention is depicted. In this embodiment, the hemostasis band 84 and wrist splint 82, as discussed above, are provided in one unitary structure 80. In this embodiment, any combination of the previously disclosed wrist splints and hemostasis bands can be combined together, thus, FIG. 13 is only provided as an exemplary structure. Thus, the hemostasis bands of the previous embodiments are appropriately modified to be attached to the splint 82 by any suitable means.

Figure 14:
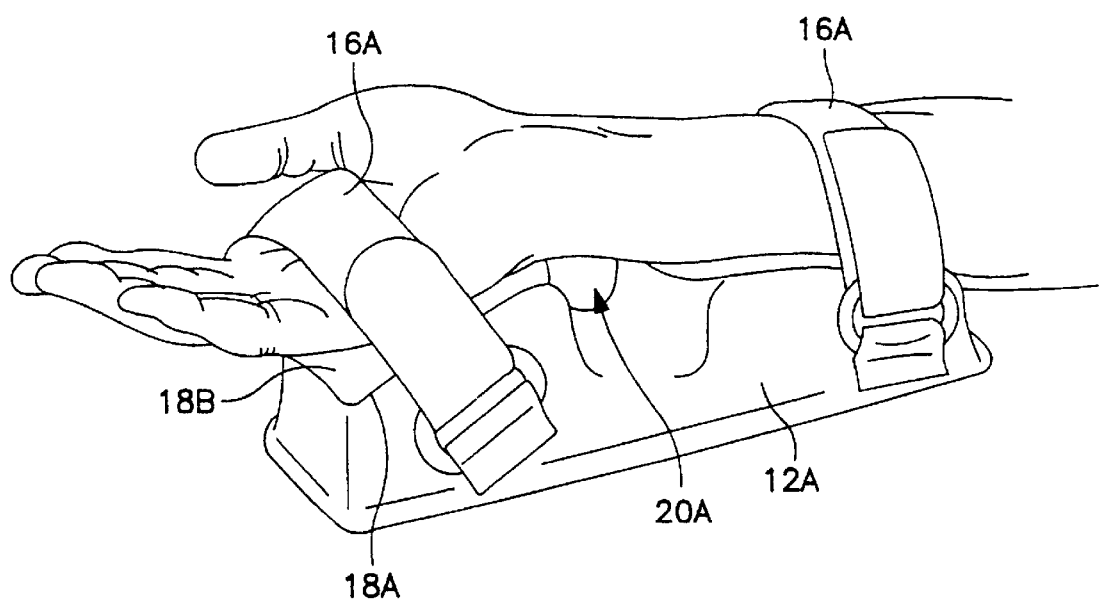
FIG. 14 is a side view of the most preferred form of the invention showing a patient's wrist held in position for a radial artery procedure.

In FIG. 14, there is illustrated the most preferred form of the invention which is based on a modification of the structure of FIG. 1. In this FIG. 14 structure the elongated member 12A is formed of a single hollow molded plastic shell having the shape illustrated. The upper surfaces 18A are preferably slightly concave and are lied with foam 18B for the patient's comfort. The straps 16A are equivalent to straps 16 in FIG. 1. The groove 20A in the top of the base 12A is similar in size and function to the groove 10 in FIG. 1.

Figure 16:
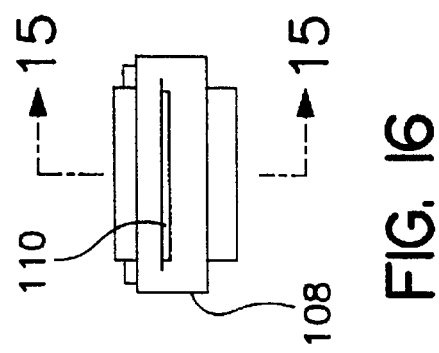
FIGS. 15 and 16 are sectional views of the most preferred form of hemostasis band.
Figure 15:
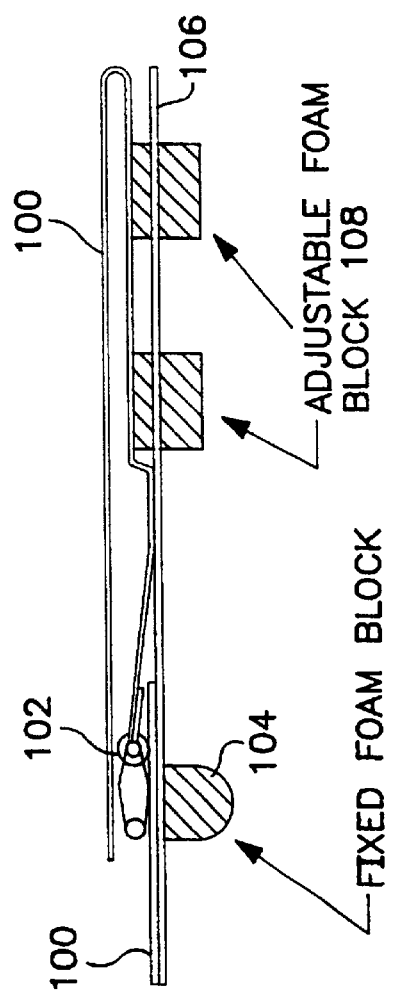

For use with the hand wrist support of the present invention the most preferred form of hemostasis band is illustrated in FIGS. 15 and 16 which are schematic illustrations of the preferred structure wherein the Velcro strap is shown in section at 100, with the buckle illustrated at 102. A fixed foam block 104 is secured to the strap below the buckle 102. Also secured to the strap 100 adjacent the buckle is a rigid plastic strip 106 having a smooth surface. Carried on strip 106 is a pair of adjustable foam pads 108 which, by means of slits 110, can be slid along the strip 106 to their desired operating position.

The pads 108 slide along the strip 106 and keep the strip 106 off the surface of the skin. Keeping the strip 106 off the skin's surface prevents the band from acting as a tourniquet, which might compromise ulnar artery flow and/or venous return. Possible positions for the support pads would be on the styloid process of the ulna and the lateral-posterior aspect of the head of the radius (see FIG. 17). The pads 108 should be positioned so that they do not occlude blood flow through the ulnar artery or the basilic and cephalic veins.

Modifications of the present invention are possible. For example the splint/hemostasis band/combined device can be formed of radio-lucent material suitable for x-ray analysis, etc., provided, of course, that such material meets the above-mentioned requirements for sterility. It should also be noted the present invention is equally applicable to either the left or right extremities. Further modifications will become apparent to those skilled in the art, and all such modifications are deemed within the scope of the present invention.

Advantages

Advantageously, the wrist splint of the present invention is shaped to position the hand and wrist in a hyperextended state during radial procedures and to keep the hand and wrist immobilized during the procedure. Also advantageously, the splint of the present invention positions the hand and wrist in such a manner so as to extend the radial artery for simple, safe ingress during radial artery procedures. In addition, the present invention provides a hemostasis band which is advantageously designed to apply pressure directly to the puncture wound site of the radial artery to prevent bleeding and permit closure of the wound. Also advantageously, the hemostasis band has features that permit sufficient pressure to be applied to the radial artery (so that the wound can close) while maintaining blood flow through the radial artery or, for that matter, through the ulnar artery or venous return. The wrist splint and homeostasis band can also be combined into one unitary device having all the advantageous features described above.

We claim:

1. A hand/wrist positioning splint to keep the hand positioned for radial artery access and to permit application of a hemostasis band to apply pressure to the radical artery puncture site to permit closing of said puncture site;
   a rigid structure (12) for positioning a patient's hand and wrist in a fixed hyperextended state with the patient's radial artery exposed, said structure having a distal end surface (14) to support a patient's hand, palm up, the end surface extending downwardly from the wrist position to make a first fixed angle (26) with a horizontal plane;
   the rigid structure having a wrist/forearm support surface also extending downwardly from the wrist position to make a second fixed angle (24) with a horizontal plane;
   straps (16) for securing the hand and wrist/forearm in fixed position on said rigid structure; and
   an opening (20) in the wrist/forearm surface of said rigid support below the point of arterial access to permit application of a hemostasis band to the radial arterial puncture site.

2. The structure of claim 1, wherein said first angle (26) is on the order of 25° and said second angle (24) is on the order of 12°.

3. The structure of claim 1, wherein said rigid structure (12) comprises a hollow rigid shell having a flat base and a foam upper surface.

4. The structure of claim 1, which includes a hemostasis band wherein the hemostasis band has a buckle (22) for securing the band to the patient's wrist; and
   a pressure pad adjacent the buckle for applying hemostasis pressure to the puncture site.

5. The structure of claim 1, wherein said the first angle (26) and second angle (24) are so related that the top of the hand and the top of the forearm make an angle on the order of 40°.

6. A hemostasis band having a buckle for securing the band to a patient's wrist;
   a pressure pad fixedly positioned to and underlying the buckle for applying hemostasis pressure to the puncture site; and
   at least two additional pads adjustable along said band for spacing a portion of said band away from the wrist to prevent tourniquet action by the hand.

7. The structure of claims 6, wherein the two additional pads (108) are supported by a smooth plastic portion of said band to permit easy adjustment of the pads along the band.

8. The structure of claim 7, wherein a hook and loop band (100) having a loop buckle is secured to one end thereof, a separate smooth plastic strip (106) is secured to the inner surface of the band adjacent the loop buckle and separate from the hook and loop band throughout most of its length, the hemostasis pad being fixedly secured to the inner surface of the smooth plastic strip adjacent the loop buckle and the two additional pads being slidably supported on the smooth plastic strip.

9. The structure of claim 8, wherein the additional pads (108) are mounted on the plastic strip by passing the plastic strip through a transverse slot in each of said two pads.

10. A hemostasis band having a buckle for securing the band to a patient's wrist;
    a pressure pad underlying the buckle for applying hemostasis pressure to the puncture site; and
    at least two additional pads adjustable along said band for spacing a portion of said band away from the wrist to prevent tourniquet action by the hand, said two additional pads being supported by a smooth plastic portion of said band to permit easy adjustment of the pads along the band.

11. The structure of claim 10, wherein a hook and loop band having a loop buckle is secured to one end thereof, a separate smooth plastic strip is secured to the inner surface of the band adjacent the loop buckle and separate from the hook and loop strip throughout most of its length, the hemostasis pad being fixedly secured to the inner surface of the smooth plastic strip adjacent the loop buckle and the two additional pads being slidably supported on the smooth plastic strip.

12. The structure of claim 11, wherein the additional pads are mounted on the plastic strip by passing the plastic strip through a transverse slot in each of said two pads.

13. A hand/wrist positioning splint to keep the hand positioned for radial artery access and to permit application of a hemostasis band to apply pressure to the radical artery puncture site to permit closing of said puncture site;
    a rigid structure for positioning a patient's hand and wrist in a fixed hyper-extended state with the patient's radial artery exposed, said structure having a distal end surface to support a patient's hand, palm up, the end surface extending downwardly from the wrist position to make a first fixed angle with a horizontal plane;
    the rigid structure having a wrist/forearm support surface also extending downwardly from the wrist position to make a second fixed angle with a horizontal plane;
    straps for securing the hand and wrist/forearm in fixed position on said rigid structure; and
    an opening in the wrist/forearm surface of said rigid support below the point of arterial access to permit application of a hemostasis band to the arterial puncture site.

14. The structure of claim 13, wherein said first angle is on the order of 25° and said second angle is on the order of 12°.

15. The structure of claim 13, wherein said rigid structure comprises a hollow rigid shell having a flat base and a foam upper surface.

16. The structure of claim 13, which includes a hemostasis band wherein the hemostasis band has a buckle for securing the band to the patient's wrist; and
    a pressure pad adjacent the buckle for applying hemostasis pressure to the puncture site.

17. The structure of claim 13, wherein said first angle and second angle are so related that the top of the hand and the top of the forearm make an angle on the order of 40°.

* * * * *